United States Patent [19]

Hurlock et al.

[11] 4,010,142

[45] Mar. 1, 1977

[54] PURIFICATION OF ACRYLAMIDE VIA CRYSTALLIZATION WITH CENTRIFUGAL LIQUOR SEPARATION

[75] Inventors: John R. Hurlock, Hickory Hills; Kenneth G. Phillips, River Forest, both of Ill.

[73] Assignee: Nalco Chemical Company, Oak Brook, Ill.

[22] Filed: Dec. 15, 1975

[21] Appl. No.: 641,062

[52] U.S. Cl. .................................... 260/561 N
[51] Int. Cl.$^2$ ............................... C07C 103/133
[58] Field of Search ........................ 260/561 N

[56] References Cited

UNITED STATES PATENTS

| | | | |
|---|---|---|---|
| 3,324,180 | 6/1967 | Beer et al. | 260/561 N |
| 3,902,855 | 9/1975 | Lynch | 260/561 N |

FOREIGN PATENTS OR APPLICATIONS

| | | |
|---|---|---|
| 897,209 | 5/1962 | United Kingdom |

OTHER PUBLICATIONS

Kirk–Othmer, Encyclopedia of Chemical Technology, vol. 1 (1963), pp. 279–280.
Weissberger, Techniques of Organic Chem., vol. III (1950), Interscience Publishers, N.Y., N. Y.

*Primary Examiner*—Arthur P. Demers
*Attorney, Agent, or Firm*—John G. Premo; John S. Roberts

[57] ABSTRACT

Removal of organic impurities from a dilute solution of aqueous acrylamide is achieved by
 a. vacuum stripping of the aqueous acrylamide at > 25° to 50° C to concentrate the aqueous solution to about 80% acrylamide;
 b. cooling to about 25° C to produce a slurry of acrylamide crystals;
 c. centrifuging the acrylamide crystals to express mother liquor and forming a crystal cake of acrylamide crystals;
 d. washing the crystal cake with water wash to produce an aqueous rinse liquor; and
 e. recycling the mother liquor and rinse liquor to vacuum stripping, step (a). The recycling of mother liquor from step (c) and rinse liquor from step (d) is effected $n$ times where $n = 4$–20.

This purifying process serves to remove certain nonvolatile and non-ionic organic impurities from the acrylamide monomer which are principally trieneamide together with small amounts of valeramide-$\Delta$-1:3-diene and $\delta$-cyano-valeramide-$\Delta$-ene. The present process is designed to lower the concentration of trieneamide to a maximum value of 7.5 ppm. These organic impurities in the past had interfered with the activity of and the production of water-soluble homopolymers and copolymers from the acrylamide monomer.

7 Claims, No Drawings

PURIFICATION OF ACRYLAMIDE VIA CRYSTALLIZATION WITH CENTRIFUGAL LIQUOR SEPARATION

The present invention relates to the purification of dilute aqueous solutions of acrylamide monomer as they are produced by the hydration of acrylonitrile in the presence of a metal catalyst. In recent years reduced copper oxides, among others, have specially been utilized as a basis for a catalyst for this hydration and the following prior art relating to hydration of acrylonitrile is cited:

U.S. Pat No. 3,597,481
U.S. Pat. No. 3,631,104
U.S. Pat. No. 3,642,894
U.S. Pat. No. 3,642,643
Canadian Pat. No. 839,384 (1972)

Additionally, the following patents are cited as prior art related to the present invention:

U.S. Pat. No. 2,892,870 Matile — purifying urea by centrifuge separation of impurities and crystallizing urea.

U.S. Pat. No. 3,689,558 Modeen et al. — inhibition of polymerization in hydration of acrylonitrile by use of cupferron, a nitrosophenol or a tri(lower alkyl)amine.

U.S. Pat. No. 3,902,855 Lynch — countercurrent multiple recrystallization of acrylamide.

U.S. Pat. No. 3,917,693 Asano et al. — concentrating an aqueous acrylamide solution by distillation.

British Pat. No. 897,209 — page 3, column 1, teaches parameters of preferred temperature (0°–60° C) with cooling to initiate crystallization.

The solutions produced by the hydration of acrylonitrile to acrylamide are usually dilute solutions and in order to utilize acrylamide in crystalline or dry form, water must be removed by evaporative techniques to supersaturate the acrylamide solution. Coupled with the water removal, another problem faced is that in many of the acrylamide monomer aqueous solutions utilized as a starting point in this invention, there are present minor amounts of certain organic impurities probably derived from the acrylonitrile. The most predominant impurity appears to be trieneamide with a minor quantity of valeramide$\Delta$-1:3-diene and $\delta$-cyano-valeramide-$\Delta$-ene. These impurities are non-volatile and non-ionic and are set out below by formula.

at values of ~86% overall yield. The sequential process set out below is specially designed for a dilute aqueous acrylamide monomer solution derived from a metal catalyst assisted hydration of acrylonitrile.

a. The acrylamide monomer solution produced from acrylonitrile is inhibited by vinyl monomer inhibitors such as a copper salt and concentrated under vacuum stripping where the temperature did not exceed 50° C. Vacuum stripping may be accomplished at 25° C and up to 50° C. Stripping was continued until the acrylamide concentration in the pot or container was about 80%.

b. This concentrated acrylamide was cooled to about 25° C and a thick slurry of small acrylamide crystals formed from the supersaturated solution.

c. The slurry of crystals from step (b) was poured into a basket centrifuge with glass cloth liner and the centrifuge was accelerated to about half speed or 2200–2600 G's to force out mother liquor from the crystals and produce a crystal cake. It is an object of the invention to produce a uniform hollow cylinder type crystal cake which is available for further washing and, as noted above, a basket-type centrifuge is preferred. The magnitude of centrifugal force to accomplish the formation of the cake is commonly expressed in multiples of gravity, and a preferred force or G is set out above. Any convenient centrifuge apparatus may be used and those of the basket- or sedimentation-type are preferred. An amplification of alternatives is set out in Perry's *Chemical Engineers Handbook*, 4, page 19–86 and particularly basket filters described at pages 19–93 through 19–97, designated Filtering Centrifugals.

d. The crystal cake from the centrifuge procedure in step (c) was washed and the centrifuge was re-accelerated to about 4100 rpm to express the wash or rinse liquor.

e. The mother liquor from step (c) and the wash liquor from step (d) were recycled to step (a) and this procedure was utilized $n$ times where $n = 4$–20 cycles.

Since the great part of the organic impurities was trieneamide, it was found that about 80% was separated in 4 cycles and 90% in 10 cycles and that 4 cycles gave a maximum of 7.5 ppm of trieneamide, which value allows for a satisfactory activity for a polymer produced from the purified acrylamide monomer. The term "activation" is utilized here in a negative sense to express the result where the acrylamide monomer en-

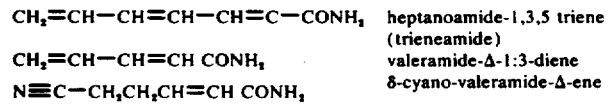

| | |
|---|---|
| $CH_2=CH-CH=CH-CH=C-CONH_2$ | heptanoamide-1,3,5 triene (trieneamide) |
| $CH_2=CH-CH=CH\ CONH_2$ | valeramide-$\Delta$-1:3-diene |
| $N\equiv C-CH_2CH_2CH=CH\ CONH_2$ | $\delta$-cyano-valeramide-$\Delta$-ene |

These substances hinder or interfere with the utilization of acrylamide monomer in producing satisfactory polymers in that subsequent homopolymerization and copolymerization of the acrylamide monomer to achieve water-soluble polymers is hindered in flocculation by the presence of these materials. It is a purpose of this invention to provide a preparation to reduce the amount of the predominant trieneamide to a maximum value of 7.5 ppm at which value it no longer affects subsequent polymerization of the acrylamide.

The present invention also has an object or a function by its cyclical nature to operate with a minimum wastage of monomer which is recovered in crystalline form tering the polymer formation loses flocculating activity and in this process the results show that certain polymers using a purified acrylamide of the present process are 8 times as effective as measured by the iron oxide replacement ratio described post in Example 1. This value has been sustained for both homopolymers and copolymers derived from acrylamide monomer.

It has been found in this process, as noted above, that an extremely satisfactory yield of purified acrylamide can be obtained which has a substantially improved purity over input acrylamide containing organic impurities which are non-volatile and non-ionic.

The results in Table I below show the present process operated through 10 cycles for the purification of acrylamide monomer, showing an overall yield of crystalline acrylamide of 86%. The starting material denoted A3 had a triene content of 82 ppm. The polymer results show the production of polymers from each cycle with the activity of the resultant polymers measured by intrinsic viscosity, Huggins Constant, and the iron oxide replacement ratio, $R/R_o$. It is noted that for the input acrylamide monomer having 82 ppm of trieneamide, an average replacement ratio is 4.0, which is unsatisfactory. It is further noted that the average $R/R_o$ value for 10 cycles was 0.47 and any value for $R/R_o$ for 1.0 or less being equivalent to a trieneamide concentration of ≤ 7.5 ppm is satisfactory.

mately 80%. The concentrate was then cooled in the tap water jacketed flask with vigorous agitation until the temperature was lowered to 25° C and a thick slurry of small acrylamide crystals had formed. The slurry was then poured into a 12-inch stainless steel basket centrifuge having a glass cloth liner. The centrifuge was initially spun at low speed so that the crystal cake could be shaped as with a spatula into a uniform hollow cylinder with radii of 11.5 and 13.75 cm. Then the centrifuge was accelerated to approximately 4100 rpm (half speed) where under the force of 2200 to 2600 G's the remaining expressable mother liquor was spun from the crystals.

At this point in the process the crystal cake and the mother liquor were both weighed and the mother li-

TABLE I

Purification of Acrylamide Via Crystallization With Centrifugal Liquor Separation

| | INPUT STREAMS | | | | RECYCLED AND INTERNAL STREAMS | | | | | | | | |
|---|---|---|---|---|---|---|---|---|---|---|---|---|---|
| | Acrylamide | | Wash Water | | Mother Liquor | | | Unwashed Crystal | | | Rinse Liquor | | |
| Cycle No. | Total Wt | Acam Wt | Wt. | Displ No. | Total Wt | Acam Wt | Triene G.C. | Total Wt | Acam Wt | Mother Liquor | Total Wt | Acam Wt | Triene G.C. |
| A3 | | | | | | | | | | | | | |
| 1 | 4762 | 1924 | 100 | 1.8 | 1720 | 1050 | | 846 | 791 | 141 | 157 | 66 | |
| 2 | 1726 | 697 | | 2.4 | 1510 | 1006 | | 895 | 854 | 123 | 193 | 97 | |
| 3 | 1802 | 728 | | 1.3 | 1170 | 799 | | 1020 | 941 | 249 | 171 | 88 | |
| 4 | 2031 | 820 | | 2.1 | 1390 | 908 | trace | 830 | 783 | 136 | 198 | 108 | |
| 5 | 1980 | 800 | | 4.0 | 1383 | 899 | | 845 | 820 | 134 | 202 | 107 | |
| Avg 1-5 | 1885 | 761 | 100 | | 1435 | 932 | | 887 | 838 | 140 | 184 | 93 | |
| 6 | 1620 | 713 | 200 | 5.1 | 792 | 493 | | 1155 | 1116 | 103 | 371 | 188 | |
| 7 | 2784 | 1125 | | 6.25 | 1070 | 657 | | 1130 | 1098 | 83 | 357 | 173 | |
| 8 | 2102 | 925 | | 8.0 | 1125 | 705 | .495 | 990 | 965 | 67 | 357 | 173 | trace |
| 9 | 2296 | 928 | | 3.6 | 956 | 589 | | 1240 1184 | 146 | 370 | 179 | | |
| 10 | 2488 | 1005 | | 3.2 | 1038 | 631 | .695 | 1180 | 1117 | 161 | 368 | 180 | .026 |
| Avg 6-10 | 2258 | 939 | 200 | 5.2 | 996 | 615 | | 1139 | 1096 | 112 | 365 | 179 | |
| TOTAL | 23591 | 9665 | 1500 | | 12154 | | | 10131 | 9669 | 1343 | | | |
| % | | 100 | | | | | 6.5 | | | | | | 1.9 |

| | OUTPUT STREAMS | | | | | | | COPOLYMER 70/30 ACRYLAMIDE/ACRYLIC ACID | | | | |
|---|---|---|---|---|---|---|---|---|---|---|---|---|
| | Condensate | | Washed Crystal | | | Losses | | (λ) dl/gm | | Huggins Const | | Iron Oxide |
| Cycle No. | Total Wt | Acam Wt | Total Wt | Acam Wt | Triene * | $H_2O$ | Acam | Pre-Heat | Post Heat | Pre-Heat | Post Heat | Replacement Ratio (Post) |
| A3 | | | | | 82 ppm | | | 28.8 | 20.4 | .43 | 0.51 | 4.0 |
| 1 | 2165 | — | 765 | 725 | .0058 | −55 | −83 | 28.8 | 30.6 | .43 | .31 | .41 |
| 2 | 1180 | — | 805 | 757 | .0057 | −105 | +51 | 25.1 | 29.6 | .40 | .25 | .35 |
| 3 | 1280 | — | 904 | 853 | .0073 | −39 | −87 | 27.0 | 27.2 | .43 | .42 | .45 |
| 4 | 1160 | — | 715 | 675 | .0057 | +1 | −11 | 27.3 | 29.2 | .48 | .44 | .45 |
| 5 | 1315 | — | 770 | 713 | .0028 | −38 | −91 | 26.1 | 25.3 | .46 | .50 | .25 |
| Avg 1-5 | 1259 | — | 799 | 745 | — | −47 | −44 | | | | | |
| 6 | 1194 | 12 | 975 | 928 | .0079 | −62 | −97 | 24.0 | 25.3 | .42 | .43 | .45 |
| 7 | 1725 | 14 | 960 | 925 | .0069 | −25 | −40 | 31.5 | 30.9 | .27 | .34 | .35 |
| 8 | 1380 | 22 | 835 | 792 | .0067 | −22 | −58 | 30.1 | 31.9 | .27 | .39 | .45 |
| 9 | 1567 | 19 | 1065 | 1005 | .0166 | −9 | −8 | 20.3 | 22.4 | .61 | .47 | .85 |
| 10 | 1604 | 19 | 1010 | 937 | .0098 | +16 | −4 | 25.8 | 27.3 | .42 | .53 | .55 |
| Avg 6-10 | 1494 | 17 | 969 | 917 | .0120 | −20 | −41 | | | | | .47 |
| TOTAL | 14570 | 86 | 8312 | | .075 | 338 | 428 | | | | | |
| % | | | | 86.0 | | | 4.4 | | | | | |

*Trieneamide by Tolerance Test and Material Balance

EXAMPLE 1

A dilute aqueous acrylamide monomer solution (2,000 grams as acrylamide) was inhibited with 25 ppm (BOM) of a copper salt and concentrated by vacuum stripping in a steam-jacketed 3 liter glass resin flask. Vacuum was adjusted so that the pot temperature did not exceed 50° C. Stripping was continued until the weight of the recovered condensate indicated that the acrylamide concentration in the flask was approxiquor was analyzed by G.C. for acrylamide and in some cases for trace impurities such as trieneamide.

Each acrylamide crystal cake was washed with 100 or 200 grams of ice-chilled deionized water (4° C) and the centrifuge during the water wash was accelerated to 4100 rpm. Wash water was applied in a flat fan-shaped spray directly onto the inner surface of the crystal cake. After all the rinse centrifugate had been spun from the crystals, the rinse liquor was weighed, analyzed for acrylamide (G.C.) and recycled to the concentrator for the next cycle.

A total of 10 cycles of the proposed total liquor recycle were run and at the end of 10 cycles an overall yield of crystalline acrylamide was 86% of the monomer input. In addition, the average iron oxide replacement ratio, which is $R/R_o$, over the 10-cycle run was 0.47. This ratio is a ratio between the test polymer and a standard polymer derived from purified acrylamide monomer with a trieneamide value $\lesssim$ 7.5 ppm. Thus, the ratio $R/R_o$ indicates relationship between test polymer, R, and standard polymer, $R_o$, derived from purified acrylamide wherein the trieneamide content $\leq$ 7.5 ppm. In the present case where the replacement ratio for the feedstock acrylamide is 4.0 and the replacement ratio of purified acrylamide after 10 cycles is 0.47, this demonstrates an improvement relating to the troublesome unsaturate of about 9:1. Additionally, it was found that there was a reduction in trieneamide content from about 82 ppm to $\leq$ 7.5 ppm.

In summary, the iron oxide replacement ratio test is a relative flocculation test for polymers which measures the ability to floc about iron oxide ($Fe_2O_3$) particles. The organic impurities hinder the activity of the polymer and increase the time of settling. The $R/R_o$ fraction or replacement is the value necessary to replace or substitute for a polymer derived from pure acrylamide monomer (i.e., with a maximum of 7.5 ppm of trieneamide.)

EXAMPLE 2A

Polymer Properties with Varying Levels of Trieneamide

The polymer is a copolymer 70/30 of polyacrylamide/polyacrylic acid.

| Trieneamide ppm | Intrinsic Viscosity dl/gram | Iron Oxide Replacement Ratio |
|---|---|---|
| None | 31.4 | 0.60 |
| 7.5 | 25.4 | 0.40 |
| 15 | 20.4 | 1.0 |
| 80 | 15.7 | 3.5 |

The above results show the increasing value of trieneamide in the polymer is reflected in increasing iron oxide replacement ratios and thus decreased activity of the polymer.

EXAMPLE 2B

Polymer Properties Showing Variation by Dilution with Impure Acrylamide Used to Prepare Polymer

| Polymer | Acrylamide % | as triene | dl/gm | $R/R_o$ |
|---|---|---|---|---|
| A* | 0 | 7.5 ppm | | 0.6 |
| B | 25 | 20 ppm | 23.1 | 1.0 |
| C | 50 | 41 ppm | 22.4 | 1.5 |
| d | 100 | 82 ppm | 20.4 | 4.0 |

*Pure acrylamide which is gradually replaced by impure acrylamide used to prepare a 70/30 polyacrylamide/polyacrylic acid polymer.

Run A, which was 0 diluted with impure acrylamide was prepared as follows:

This preparation was exemplary of A-D above and in the present Run A the acrylamide utilized was 100% pure. In the subsequent Runs B-D, increasing amounts of this pure acrylamide was diluted with increasing amounts of impure acrylamide.

| Reagents: | |
|---|---|
| Isopar M (Exxon, isoparaffin solvent) | 155.28 grams |
| Tween 61 (Polyoxyethylene(4)-sorbitan monostearate, ICI United States) | 4.8 grams |
| Span 80 (Sorbitan monostearate, ICI United States) | 7.2 grams |
| Pure acrylamide (analysis 7.5 ppm trieneamide) | 114.24 grams |
| $H_2O$ DI | 218.36 grams |
| Acrylic acid | 48.6 grams |
| 50% NaOH | 53.8 grams |
| Versene $Na_4$ | 1.5 grams |

All the reagents were charged into the reactor and stirred at 900 rpm. The emulsion was spurged with 2000 cc/min. of nitrogen and heated to 45° C. The vinyl polymerization catalyst was added, maintaining the nitrogen blanket and the reaction sequence was as below.

The reactor was heated 2½ hours at 47.5° C $\pm$ 0.5° C and then the temperature was raised to about 51° C. In a second heating stage the temperature was maintained at 52° C for 2 hours. The temperature in the reaction was then raised to about 57° C and in a third heating stage the temperature was maintained at 56°–58° C for two hours. The total time of heating to achieve polymerization was 6½ hours. At this point a 12.0 gram sample was withdrawn which exhibited $\eta$ 30.6 dl/gram and Huggins Constant 0.24. Finally the latex was heated for one hour at 75°–77° C and 530 grams of latex was recovered. This final sample showed $\eta$ 31.4 dl/gram and Huggins Constant 0.27. It also showed an iron replacement ratio of 0.60.

We claim:

1. A method for purifying an aqueous solution of acrylamide from organic impurities produced by the catalytic hydration of acrylonitrile to acrylamide which comprises:
   a. concentrating said aqueous solution by vacuum stripping in the range >25° C to 50° C to produce an acrylamide concentration of about 80 percent;
   b. cooling to about 25° C to produce a slurry of acrylamide crystals;
   c. centrifuging said acrylamide crystals to express mother liquor and to produce a crystal cake of acrylamide;
   d. washing crystal cake with water wash to produce an aqueous rinse liquor; and
   e. recycling the mother liquor and aqueous rinse liquor to the vacuum stripping, step (a), for n times where $n = 4$–20.

2. The method of claim 1 wherein $n = 4$.
3. The method of claim 1 wherein $n = 10$.
4. The method of claim 1 wherein $n = 20$.
5. The method of claim 1 wherein the centrifuging to express mother liquor is carried out under a force of about 2200–2600 G's.
6. The method according to claim 1 wherein said organic impurities consist of a mixture of a major amount of trieneamide and minor amounts of valeramide-$\Delta$-1:3-diene and $\delta$-cyano-valeramide-$\Delta$-ene.
7. The method according to claim 1 wherein the amount of trieneamide is reduced to a maximum value of 7.5 ppm.